United States Patent [19]

Beall

[11] 4,114,421

[45] Sep. 19, 1978

[54] APPARATUS FOR MEASURING THE CONCENTRATION OF IMPURITIES WITHIN A SUBSTANCE

[75] Inventor: William R. Beall, Glendale, Calif.

[73] Assignee: Baker International Corporation, Orange, Calif.

[21] Appl. No.: 775,526

[22] Filed: Mar. 8, 1977

[51] Int. Cl.² ............................................. G01N 25/06
[52] U.S. Cl. .................................................... 73/17 R
[58] Field of Search ..................... 73/17 A, 17 R, 15 B

[56] References Cited

U.S. PATENT DOCUMENTS

| 2,669,863 | 2/1954 | Shapiro | 73/17 |
|---|---|---|---|
| 3,233,446 | 2/1966 | Ceglia | 73/17 |
| 3,267,728 | 8/1966 | Solomons | 73/17 |
| 3,373,607 | 3/1968 | Schoenlaub | 73/17 |
| 3,447,358 | 6/1969 | Crespin | 73/17 |
| 3,477,274 | 11/1969 | Wald et al. | 73/15 |
| 3,587,293 | 6/1971 | Bowers | 73/17 |
| 3,677,064 | 7/1972 | Simpson | 73/17 |

OTHER PUBLICATIONS

Taylor, "Op-Amp Scale Expander etc." in Electronic Design, vol. 23, No. 21, p. 94, Oct. 1975.

Primary Examiner—Herbert Goldstein
Attorney, Agent, or Firm—William C. Norvell, Jr.

[57] ABSTRACT

An apparatus is disclosed for measuring the concentration of impurities within a substance by the measurement of the reduction in freezing point of the substance. A container containing the substance is coupled to a temperature variation means such as a solid state thermoelectric device for cooling the substance within the container. A temperature sensor such as a thermistor is mounted in thermal contact with the substance for providing a temperature sensor output in accordance with the temperature of the substance. A first amplifier is connected to the temperature sensor for providing a first amplifier output in relation to the output of the temperature sensor. A second amplifier is connected for receiving the first amplifier output to provide a second amplifier output. Control means receives the second amplifier output for controlling the thermoelectric device in accordance with a preselected standard or program. The control means may be programmed for cooling the substance at a pre-established rate of temperature change. A third amplifier is connected for receiving the first amplifier output for providing a precision third amplifier output for indicating the precise concentration of impurities within the substance. A sample and hold and timing circuit may be included to receive the third amplifier output for indicating the trend of the concentration of impurities in the substance as a function of time during a continuous chemical process.

4 Claims, 3 Drawing Figures

APPARATUS FOR MEASURING THE CONCENTRATION OF IMPURITIES WITHIN A SUBSTANCE

BACKGROUND OF THE INVENTION

1. Field of the Invention

This invention relates to an apparatus for determining the purity of a substance by monitoring the change in a temperature dependent physical property of the substance, and more particularly, to an apparatus for monitoring the depression of the freezing point of the substance.

2. Background of the Invention

Among the most important measurements made in the chemical industry is the determination of the purity of substances such as reagent grade chemicals. Many of these chemicals are required by custom and/or law to be labeled on the basis of the purity of the product. An accurate way of determining the purity of a substance is by the measurement of the depression of the freezing point of the substance caused by the presence of the impurities. Raoult's Law states that the inclusion of impurities within a substance results in a freezing point depression and a boiling point elevation of the impure substance compared to the pure substance. The magnitude of these changes is dependent on the concentration of the included impurities. The theory of Raoult's Law is explained in detail in my paper entitled "Automatic Purity Analysis by Freezing Point Measurement" presented at the 22nd International Instrumentation Symposium, May 1976, in San Francisco, Calif. The aforementioned paper is hereby incorporated by reference into the instance specification.

Probably the most common method used for determining the purity of reagent grade chemicals is the ASTM D 1015 method. Unfortunately, this method is not practical for a continuous flow system due to a prohibitive time lag between the time the samples are obtained and the time required to accurately determine the purity. Accordingly, this method is more applicable to a batch process rather than a continuous flow system.

Therefore it is an object of this invention to provide an apparatus which overcomes the aforementioned inadequacies of the prior art measurements and provides an improvement which is a significant contribution to the advancement of the art of purity analysis.

Another object of this invention is to provide an apparatus for measuring the concentration of impurities within a substance by the measurement of the reduction in the freezing point of the substance which is readily applicable to a continuous flow chemical process and provides several accurate determinations of purity per hour.

Another object of this invention is to provide an apparatus for measuring the concentration of impurities within a substance by the measurement of the reduction in the freezing point of the substance incorporating a cell having an input and an output conduit for receiving and discharging the substance and including temperature variation means such as a solid state thermoelectric device for varying the temperature of the substance within the cell.

Another object of this invention is to provide an apparatus for measuring the concentration of impurities within a substance by the measurement of the reduction in freezing point of substance including a thermistor probe established within the cell for sensing the temperature of the substance and a novel amplifier module for providing a control output capable of controlling the temperature of the substance and a precision output for indicating the precise concentration of impurities within the substance.

Another object of this invention is to provide an apparatus for measuring the concentration of impurities within a substance by the measurement of the reduction in the freezing point of the substance wherein the control means may be programmed for receiving a new sample of the substance into the apparatus at pre-established intervals of time for providing plural tests of the substance for indicating the change in concentration of impurities within the substance as a function of time.

Another object of this invention is to provide an apparatus for measuring the concentration of impurities within a substance by the measurement of the reduction in the freezing point of the substance including a thermoelectric device interposed between the substance container and a heat sink for transferring heat from the substance in the container to a circulating cooling liquid within the heat sink.

Another object of this invention is to provide an apparatus for measuring the concentration of impurities within a substance by the measurement of the reduction in the freezing point of the substance which provides an output which is compatible with computers, recorders and the like.

Other objects and a fuller understanding of this invention may be had by referring to the summary of the invention, the description and the claims, taken in conjunction with the accompanying drawings.

SUMMARY OF THE INVENTION

The invention may be incorporated into an apparatus for measuring the concentration of impurities within a substance wherein the concentration of impurities is related to a change in the temperature component of a physical property of the substance. The physical property of the substance may be a reduction in the freezing point or the raising of the boiling point of the substance relative to the freezing and boiling point of a pure substance. The invention includes temperature sensor means for providing a temperature sensor output in accordance with the temperature of the substance. A first amplifier means is connected for receiving the temperature sensor output to provide a first amplifier means output in accordance with the temperature sensor output. A second amplifier means is connected for receiving the first amplifier means output to provide a second amplifier means output. Control means controls the temperature of the substance in accordance with the second amplifier means output and in accordance with a predetermined standard. A third amplifier means is connected for receiving the first amplifier means output to provide a third amplifier means output indicative of the concentration of the impurities contained within the substance.

More specifically, the temperature sensor means may take the form of a temperature sensor such as a thermistor probe for providing a change in electrical resistance in accordance with the change in temperature thereof. An input resistor is connected in series with the temperature sensor across a source of electrical potential. First connecting means connects the junction of the temperature sensor and the input resistor to the input of the first amplifier. In one embodiment, the temperature sensor is directly connected to the first amplifier means which is operating as a voltage follower. Further in this specific example, the second amplifier means is an operational amplifier having an inverting and a non-inverting input. Second connection means connects the first amplifier means output to one of the inverting and non-inverting inputs with variable voltage source means connected to the other of the inverting and non-inverting inputs of the second amplifier. The control means includes a programmer for changing the temperature of the substance at a pre-established rate of temperature change in accordance with a preselected programmed temperature variation.

The temperature variation means may incorporate a solid state thermoelectric device. The substance is received within a container comprising a cell having an input and an output conduit for receiving and discharging the substance from a fluid carrying conduit of a chemical system. A conduit valve controls the flow of the substance through one of the input and output conduits. The solid state thermoelectric device is interposed between the container and a heat sink for transferring heat from the substance in the container to the heat sink. The heat sink may take the form of a housing in thermal contact with the thermoelectric device and adapted to receive a circulating cooling liquid.

The third amplifier means comprises a third and fourth operational amplifier, each having an inverting and a noninverting input. Third connecting means connects the first amplifier output to one of the inputs of the third amplifier. Fourth connection means connects the output of the third amplifier to one of the inputs of the fourth amplifier. One of the third and fourth connection means may include variable resistance means with variable voltage source means connected to the other of the inverting and non-inverting inputs of one of the third and fourth amplifiers.

The invention also may include a sample and hold circuit connected for receiving and storing the third amplifier means output which is indicative of the concentration of the impurities in the substance. A selectable time means provides a timer means output in relation to a preselected time interval to energize the sample and hold circuit to store a new output of the third amplifier means. An indicator may be provided for indicating a plurality of outputs from the sample and hold circuit as a function of time to display the trend of the impurity concentration. The invention may include mechanical vibration means which cooperates with the container for mechanically vibrating the substance upon a preselected output for solidifying a super-cooled liquid.

This invention accordingly comprises an apparatus possessing the features, properties and the relation of elements which will be exemplified in the apparatus hereinafter described, and the scope of the invention will be indicated in the claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION

Figure 1:
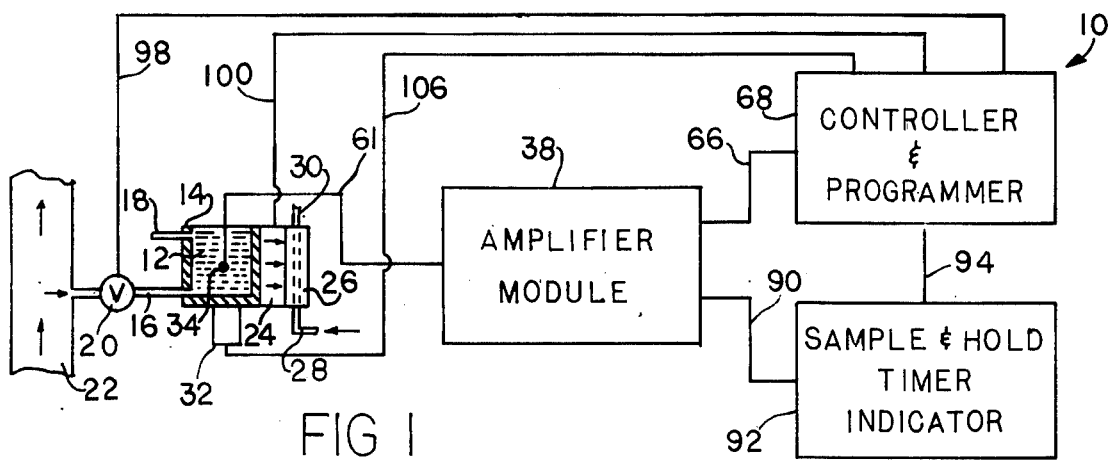
FIG. 1 is a diagram of an apparatus for measuring the concentration of impurities within a substance by the measurement of the reduction in freezing point of the substance including a container for containing the substance and the associated electronic and mechanical components shown in block form.

FIG. 1 illustrates an apparatus 10 for measuring the concentration of impurities within a substance 12 receivable within a container 14 shown as a cell. An input and output conduit 16 and 18 respectively receive and discharge the substance 12 relative to the cell 14. A control valve 20 controls the substance flow from a main conduit 22 through the input conduit 16 into the cell 14. The main conduit 22 may be a portion of a static or a continuous flow chemical process system.

Temperature variation means shown as a solid state thermoelectric device 24, is established in thermal contact with the container 14 for providing heat flow relative to the substance 12 within the container 14. Heat sink 26 is thermally coupled to the thermoelectric device 24 for heat transfer relative to the thermoelectric device 24. The heat sink 26 is shown as a housing in thermal contact with the thermoelectric device 24 and adapted to receive a circulating heating or cooling liquid through conduits 28 and 30. In this embodiment, the heat sink housing 26 receives a cooling liquid with the thermoelectric device 24 established to transfer heat from the substance 12 to the heat sink 26. However, it should be understood that the process may be reversed for determining the rise in the boiling point rather than the lowering of the freezing point of the substance. It should also be understood that plural thermoelectric devices and heat sinks may be incorporated in the preferred embodiment. A mechanical vibration means shown as a knock solenoid 32 is mounted relative to the container 14 for providing a mechanical vibration to the substance 12 within the container 14 upon activation as will be hereinafter described.

A temperature sensor means 34 is shown as a temperature sensor providing a change in electrical resistance in accordance with a change in temperature thereof. In this specific embodiment, a thermistor probe is established at the geometric center of the container 14 for monitoring the temperature of the substance 12 within the container 14. Thermistor 34 is connected by first connector means 61 to an amplifier module 38 shown as a block in FIG. 1 and in specific detail in FIG. 3.

Figure 3:
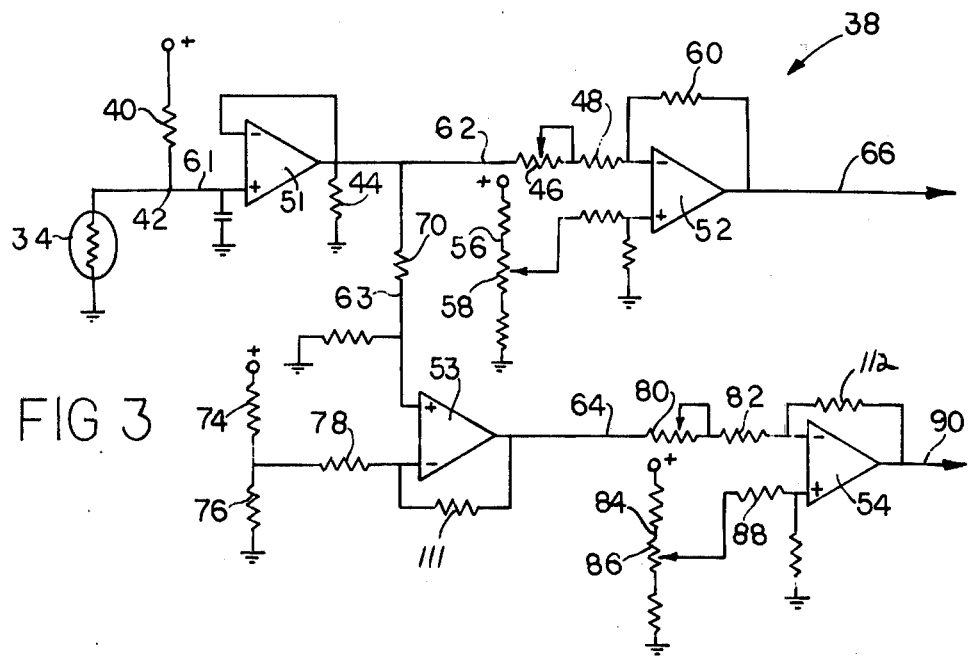
FIG. 3 is a schematic diagram of the amplifier module shown in FIG. 1.

FIG. 3 is a schematic diagram of the amplifier module 38 shown in FIG. 1. The thermistor 34 is connected in series with an input resistor 40 across an electrical potential as shown. The change in thermistor resistance is inversely related to a change in temperature of the substance 12.

The junction 42 of thermistor 34 and input resistor 40 is directly connected by the first connection means 61 to the non-inverting input of first amplifier means 51 shown as an operational amplifier. The output of first amplifier means 51 is directly coupled to the inverting input of amplifier 51 resulting in a unity gain first amplifier 51. This configuration is normally referred to as a voltage follower and isolates the input circuit comprising thermistor 34 and input resistor 40 from loading by subsequent amplifiers. The output of amplifier 51 is applied across load resistor 44 to provide a low impedance signal source for second through fourth amplifier means 52–54. The output of first amplifier means 51 is applied by second connecting means 62 in this embodiment shown as potentiometer 46 and resistor 48 to the inverting input of second amplifier means 52. The non-inverting input of second amplifier means 52 is connected to variable voltage source means 56 shown as a plurality of resistors including potentiometer 58 for providing a variable voltage source to the non-inverting input of amplifier 52. The variable voltage source means 56 provides a bias voltage for an offset null of second amplifier means 52. The gain of amplifier 52 is determined in part by the feedback resistor 60 and is normally selected to be from 0.5–30, depending upon the particular application. The output of second amplifier means 52 is applied by connector means 66 to a controller programmer 68 which will be hereinafter described.

The third amplifier means in this embodiment includes the third and fourth amplifiers 53 and 54. The third amplifier 53 is the first of a dual amplification stage comprising third and fourth amplifiers 53 and 54 for providing a precision output for indicating the concentration of impurities within the substance 12. Third connector means 63 including resistor 70 connect the output of the first amplifier means 51 to the non-inverting input of third amplifier 53. A voltage divider network comprising resistors 74 and 76 applies a substantially constant voltage through resistor 78 to the inverting input of the third amplifier 53. The selection of resistors 74 and 76 is made to provide the appropriate expanded scale offset for amplifier 54. The output of third amplifier 53 is applied by fourth connection means 64 including variable resistance means shown as a potentiometer 80 and resistor 82 to the inverting input of the fourth amplifier 54. Variable voltage means 84 including potentiomer 86 provides a variable voltage input through resistor 88 to the non-inverting input of fourth amplifier 54. The variable voltage means 84 determines the offset voltage of the output of fourth amplifier 54 which is connected through connecting means 90 to block 92 comprising a sample and hold circuit, timer and indicator shown in FIG. 1. Feedback resistor 111 and amplifier 53 are selected to define a typical fixed gain of 100 or 200. Feedback resistor 112 on amplifier 54 plus potentiometer 80 define the adjustable gain of amplifiers 53 and 54.

The output of the second amplifier 52 corresponds to a temperature variation of typically 10° C. and within a range of approximately 5° C. to approximately 50° C., whereas the output of the fourth amplifier 54 corresponds to a temperature variation of typically 1° C. and within a range of approximately 0.5° C. to approximately 5° C. Accordingly, the second amplifier output 52 is connected to the controller programmer 68 for controlling the apparatus 10 whereas the precision output from the fourth amplifier 54 is used for indicating the concentration of impurities within the substance.

The controller programmer 68 controls many of the functions associated with the measuring process. The timer within block 92 provides time signals through connector means 94 to the controller programmer 68. The controller programmer 68 may be programmed to test a new sample of the substance at specific intervals of time, for example, every 20 minutes. At a preprogrammed time, the controller programmer 68 energizes valve 20 through connector means 98 enabling the substance to flow through input conduit 16 and enter container 14. A subsequent signal on connector means 100 energizes thermoelectric device 24 for cooling the substance 12 within the container 14. The programmer can be preprogrammed for a specific cooling rate selected in accordance with the particular physical characteristics of the substance under test. The controller programmer 68 may also energize a solenoid valve (not shown) for supplying cooling liquid through conduits 28 and 30 to heat sink 26.

Figure 2:
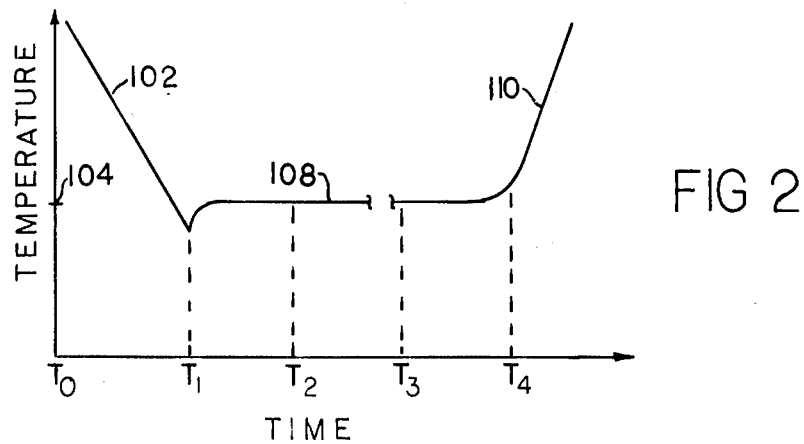
FIG. 2 is a graph of a freezing point curve showing temperature as a function of time for the substance within the container in FIG. 1.

FIG. 2 is a freezing point curve showing temperature as a function of time for the substance 12 within the container 14. The slopw of the substantially linear region 102 represents the cooling rate of the substance which is controlled by the controller programmer 68. This slope may be varied by the operator for various physical substances under investigation. Many substances continue to cool below the freezing temperature represented by the level 104 and pass into a super-cooled condition. At time $T_1$, the controller programmer 68 provides a signal on connector means 106 for energizing knock solenoid 32 for mechanically vibrating the super-cooled substance. Immediately after this mechanical vibration, the substance changes from a liquid state $(T_0-T_1)$ to a liquid-solid $(T_1-T_2)$, causing the temperature within the substance to increase to an equilibrium temperature which is the true freezing point of the substance. The substance remains at the equilibrium freezing level 108 while changing from a liquid-solid state $(T_1-T_2)$ to a solid state $(T_2-T_3)$. The cooling power may be programmed to shut off at some point in time when the substance is at equilibrium. After the substance has reached the equilibrium temperature, generally in the $T_1-T_2$ range, the controller programmer 68 energizes the sample and hold circuit 92 through connector means 94 to receive the output from the fourth amplifier 54. The indicator within block 92 indicates the precise freezing point of the substance 12 at the equilibrium level 108. The indicator means is also capable of indicating a plurality of sequential outputs of the sample and hold circuit as a function of time to indicate the history of the concentration of the impurities within the substance. Accordingly, the concentration of impurities for a plurality of past samples may be indicated as a function of time to relate the progress of the chemical process refining the substance. A comparator circuit may be incorporated in the block 92 for providing a comparator output when the concentration of impurities equals a pre-established level. The output of the comparator may be used for terminating the chemical process or filling containers for distribution or the like. Termination of the signal on connector 100 results in the substance changing state from the solid state $(T_2-T_3)$ to the liquid-solid state $(T_3-T_4)$. Continued addition of heat will cause the substance to again return to the liquid state $(T_4)$ along a heating curve 110.

The foregoing has described an apparatus which is capable of use with a continuous or static chemical process. The apparatus furnishes accurate indications of the concentration of impurities within a substance and provides several accurate determinations of purity per hour. A typical error of ±0.0001° C. correlates to an error of 0.002 mole % over a range of 98–100 mole % purity.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of the parts and of the components and the combination and arrangement of parts and of the components may be resorted to without departing from the spirit and scope of the invention.

Now that the invention has been described:

What is claimed is:

1. An apparatus for measuring the concentration of impurities within a substance by the measurement of the reduction in freezing point of the substance, comprising in combination:

container means for receiving the substance;
   said container means including a cell having an input and an output conduit for receiving and discharging the substance with a conduit valve means controlling the flow of the substance through said conduits;
   temperature variation means established for changing the temperature of the substance within said container means;
   said temperature variation means including a thermoelectric device interposed between said container means and heat sink means for transferring heat from the substance in said container means to said heat sink means;
   temperature sensor means mounted in thermal contact with the substance for providing a change in electrical characteristic in relation to a change in the temperature of the substance;
   first amplifier means connected to said temperature sensor means for providing a first amplifier means output in accordance with the change in electrical characteristic of said temperature sensor means;
   said first amplifier means being established for isolating said first amplifier means output from said first amplifier means input;
   second amplifier means connected for receiving said first amplifier means output to provide a second amplifier means output corresponding to the temperature variation of the substance;
   control means connected for receiving said second amplifier means output to control said temperature variation means in accordance with a preselected standard;
   third amplifier means comprising a differential amplifier having plural differential inputs and a third amplifier means output;
   means connecting said first amplifier means output to one of said plural differential inputs of said third amplifier means;
   a voltage source connected to the other of said plural differential inputs for biasing said third amplifier means to be sensitive to only a given magnitude of signal of said first amplifier means outputs; and
   said third amplifier means output being amplified relative to the output of said second amplifier means and corresponding to only a portion of the output of said second amplifier means for providing a precision indication of the reduction in freezing point of the substance to indicate the associated impurities contained therein.

2. An apparatus as set forth in claim 1, wherein said control means includes programmer means for changing the temperature of the substance at a preestablished rate of temperature change.

3. An apparatus as set forth in claim 1, including means for providing a mechanical vibration to the substance in said container means upon a preselected output of one of said second and third amplifier means.

4. An apparatus as set forth in claim 1, wherein said heat sink means includes a housing in thermal contact with a solid state therefor thermoelectric device and adapted to receive a circulating cooling liquid.

* * * * *